United States Patent [19]

Wilhelm et al.

[11] Patent Number: 4,854,934
[45] Date of Patent: Aug. 8, 1989

[54] SUBSTITUTED UREAS FOR ENNOBLING CELLULOSE FIBRES

[75] Inventors: Didier Wilhelm, Hauts de Seine; Antonio Gelabert, Val D'Oise; Alain Blanc, Paris, all of France

[73] Assignee: Societe Francaise Hoechst, Puteaux, France

[21] Appl. No.: 167,510

[22] Filed: Mar. 14, 1988

[30] Foreign Application Priority Data

Apr. 2, 1987 [FR] France ................ 87 04629

[51] Int. Cl.$^4$ .............. D06M 13/40; C07D 233/32; C07D 233/40
[52] U.S. Cl. ............................... 8/185; 8/186; 8/189; 544/318; 548/318; 548/319; 548/320; 549/370; 549/448; 564/60; 564/61
[58] Field of Search .............. 548/320, 318, 319; 544/318; 549/370, 448; 564/60, 61; 8/185, 186, 189

[56] References Cited

FOREIGN PATENT DOCUMENTS

| | | |
|---|---|---|
| 0141755 | 5/1985 | European Pat. Off. . |
| 97164 | 2/1897 | Fed. Rep. of Germany ........ 564/60 |
| 1172265 | 6/1964 | Fed. Rep. of Germany . |
| 1558244 | 2/1969 | France . |

*Primary Examiner*—Richard A. Schwartz
*Attorney, Agent, or Firm*—Browdy and Neimark

[57] ABSTRACT

They have the formula:

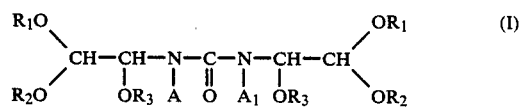

where either $R_1$ and $R_2$ are identical and represent —$CH_2R$ where $R=H$ or a $C_1$ to $C_4$ alkyl group or $R_1$ and $R_2$ together form the —$CH_2(CR_4R_4)_n$—$CH_2$ group where $n=0$ or 1, $R_4=H$ or —$CH_3$, $R_3=H$ or —$CH_2R_5$ where $R_5=H$ or a $C_1$ to $C_4$ alkyl group. A and $A_1$ are either identical and represent H or A and $A_1$ together form an ethylene, trimethylene or —$CH(OCH_2R_6)$—$CH(OCH_2R_6)$— radical where $R_6=H$ or a $C_1$ to $C_4$ alkyl group or, when $R_3=H$, a 1,2 dihydroxy-ethylene group.

They are obtained by reacting a disubstituted ethanal

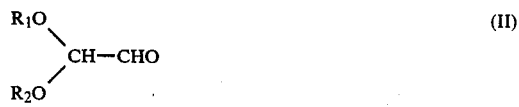

with a urea ANH—CO—NHA, followed if required by etherification with an alcohol $R_5CH_2OH$.

12 Claims, No Drawings

SUBSTITUTED UREAS FOR ENNOBLING CELLULOSE FIBRES

The present invention concerns substituted ureas, a process for their preparation and their application particularly to ennobling cellulose fibers.

The present invention has as its object substituted ureas of formula I in their racemic forms or their stereoismeric mixtures:

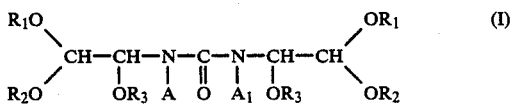

in which either $R_1$ and $R_2$ are identical and represent the $—CH_2R$ group where R represents a hydrogen atom or a $C_1$ to $C_4$ alkyl radical, or $R_1$ and $R_2$ together form a $—CH_2—(CR_4R_4)_n$ $—CH_2—$ group in which n is 0 or 1 and $R_4$ is a hydrogen atom or a methyl group, $R_3$ represents a hydrogen atom or a $—CH_2R_5$ radical in which $R_5$ represents a hydogen atom or a $C_1$ to $C_4$ alkyl group and either A and $A_1$ are identical and represent a hydrogen atom or A and $A_1$ together form an ethylene, trimethylene, or $—CH(OCH_2R_6)—CH(OCH_2R_6)—$ radical wherein $R_6$ repressents a hydrogen atom or a $C_1$ to $C_4$ alkyl group or, where $R_3$ represents a hydrogen atom, a 1,2-dihydroxyethylene group.

The expression "$C_1$ to $C_4$ alkyl" can include, for example, a methyl, ethyl, propyl, butyl, isopropyl or isobutyl radical.

The expression "in their racemic forms or their stereoisomeric mixtures" means that the asymmetric carbon atoms in products of formula I may be in their R or S configuration.

More particularly, the invention concerns products such as those defined above characterised in that, in formula (I), $R_1$ and $R_2$ are identical and represent a methyl or butyl group, $R_3$ represents a hydrogen atom, a methyl or a butyl group and either A and $A_1$ are identical and represent a hydrogen atom or A and $A_1$ together form an ethylene group, a 1,2-dimethoxyethylene group, a 1,2-dibutoxyethylene group or, when $R_3$ represents a hydrogen atom, a 1-2-dihydroxyethylene group.

Among the products the following may be particularly mentioned:
bis-1,3-(2,2-dimethoxy-1-hydroxyethyl) urea;
bis-1,3-(1,2,2,-trimethoxyethyl) urea;
bis-1,3-(2,2-dibutoxy-1-hydroxyethyl) urea;
bis-1,3-(1,2,2-tributoxyethyl) urea;
bis-1,3-(2,2-dimethoxy-1-hydroxyethyl)-2-imidazolidinone;
bis-1,3-(1,2,2-trimethoxyethyl)-2-imidazolidinone;
bis-1,3-(2,2-dibutoxy-1-hydroxyethyl)-2-imidazolidinone;
bis-1,3-(1,2,2-tributoxyethyl)-2-imidazolidinone;
bis-1,3-(2,2-diethoxy-1-hydroxyethyl)-2-imidazolidinone;
bis-1,3-(2,2-dimethoxy-1-hydroxyethyl)-4,5-dihydroxy-2-imidazolidinone;
bis-1,3-(1,2,2-trimethoxyethyl)-4,5-diomethoxy-2-imidazolidinone;
bis-1,3-(2,2-dibutoxy-1-hydroxyethyl)-4,5-dihydroxy-2-imidazolidinone;
bis-1,3-(1,2,2-tributoxyethyl)-4,5-dibutoxy-2-imidazolidinone;
bis-1,3-(2,2-dimethoxy-1-hydroxyethyl)-1H-tetrahydro-2-pyrimidinone;
bis-1,3-(1,2,2-trimethoxyethyl)-1H tetrahydro-2-pyrimidinone.

According to the invention, products having the above formula (I) can be prepared by a process which is characterised in that a disubstituted ethanal of formula II:

wherein $R_1$ and $R_2$ have the meanings given above, is reacted with a urea having formula (III):

wherein A and $A_1$ have the meanings given above, in order to obtain a product having formula IV:

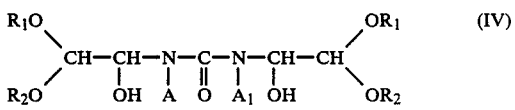

(wherein $R_1$, $R_2$, A and $A_1$ have the meanings given above) which is subsequently etherified, if desired, by normal methods using an alcohol having formula (V):

wherein $R_5$ has the meaning given above.

Ureas having the formula III are either commerically available or described in the literature.

The substituted ethanal having formula II may be obtained by the process described in French patent application No. 86 07957.

Under preferred conditions for carrying out the process of the invention, condensation of the product of formula II with the urea of formula III is carried out as follows:

at an alkaline pH, advantageously at a pH between 7 and 9, in the presence of a compatible alkaline catalyst such as sodium hydroxide or potassium hydroxide;

at a temperature of between 30° and 80° C.

The condensation may also be carried out in water or a compatible organic solvent, such as a low alcanol or in a low alcanol-water medium. The alcanol used may be chosen so as to avoid side reactions of transetherification.

In general the inventive process is carried out using stoichiometric quantities of reactants.

At the end of the condensation reaction, the substituted urea formed having formula IV is either isolated using known methods such as crystallisation, elution chromatography (see W. C. Still et al. J. Org. Chem., 1978, 43, 2923) or it is used as it is, if necessary after neutralisation of the catalyst used and elimination of the reaction solvent(s) under reduced pressure. The substituted urea having formula IV has sufficient purity in the crude state to be usable in the application described below.

If required, etherification of the hydroxyls present in the product of formula IV is carried out using normal methods for etherification of N-hydroxymethylcarbamoyl groups by the reaction of an alcanol having formula (V) in an acid medium, advantageously at a pH of between 2 and 6.5 and at a temperature of between 20° and 80° C. (see H. Petersen: Chemical Aftertreatment of Textiles, chapter V, pages 135-265, H. Mark—Wiley Interscience 1971).

Products having formula I in their racemic forms or their stereoisomeric mixtures display interesting cross-linking properties on cellulose. In particular, they can be used to endow cellulose fibres with crease and shrink resisting properties. For these applications they may be used in amounts and under operating conditions similar to those currently employed by the skilled person when using classical textile resins based, for example, on bis-1,3-(hydroxymethyl)-4,5-dihydroxy-2-imidazolidinone (see H. Peterson, loc. cit).

When applied to the ennobling of cellulose fibres, however, products having formula I have the advantage of endowing cellulose fibres with excellent usage properties without having too detrimental an influence on the fibres' mechanical properties and, above all, without the use of formaldehyde or compounds liable to liberate it. In addition, the effects obtained are reasonably permanent.

The following examples illustrate the invention without limiting it in any way.

Physical analyses were carried out using proton $1_H$ or carbon thirteen $^{13}C$ nuclear magnetic resonance (NMR) in a BRUCKER AC 200 apparatus at 200 MHz for the proton and 50 MHz for the $^{13}C$. Chemical displacements are expressed in ppm with reference to tetramethylsilane, TMS.

Certain stereoisomers exhibited small differences in chemical displacement: in such cases the chemical displacements were confirmed by recording the spectrum of the physically purified stereoisomer mixture.

Preparative high pressure liquid chromatography (HPLC) was carried out using a WATERS 600 pump and a WATERS 401 differential refractometer with a 25 cm, 2.54 mm diameter column filled with either "LICHROSORB Si60" obtainable from Merck or "POLYGOSIL C18" obtainable from Mascherey-Nagel.

EXAMPLES

Example I bis-1,3-(2,2-dimethoxy-1-hydroxyethyl)-1,3 urea 24 g (0.4 mole) of urea were dissolved, under agitation, in 96 g of a methanolic solution of dimethoxy-ethanal, 87 weight %, i.e. 0.8 mole. The solution obtained was then brought to pH 8 by addition of several drops of 2N caustic soda, then it was heated under agitation for two hours at 50° C. The methanol was driven off and the oily residue taken up in an acetonediethyloxide mixture. The desired product crystallised out, was dried, then vacuum dried to constant weight at 50° C.

Bis-1,3-(2,2-dimethoxy-1-hydroxyethyl) urea was thus obtained in the form of colourless prisms melting at 90°–110° C.

Microanalysis

|  |  | C % | H % | N % | O % |
|---|---|---|---|---|---|
| $C_9H_{20}N_2O_7$ | Calculated | 40.29 | 7.51 | 10.44 | 41.75 |
| M. Wt = 268.27 | Found | 40.8 | 7.8 | 10.6 |  |

Physical analysis

Preparative HPLC of this product on a "POLYGOSIL C18" column with a water-methanol (96.5:3.5) eluent produced the two expected diastereoisomers: the first isomer had a retention time (tr) of 244 s and the second one of 635 s (flowrate 1 cm³ per min).

The two isolated stereoisomers had the following ¹H NMR spectra in deuterated dimethylsulphoxide (DMSO $d_6$).

|  | 1st isomer, ppm | 2nd isomer, ppm |
|---|---|---|
| NH (d,2H,J = 9.4 Hz) | 6.6 | 6.6 |
| OH (d,2H,J = 5.6 Hz) | 5.53 | 5.52 |
| N—CH—O (m,2H) | 5.02 | 5.02 |
| CH (OMe)₂(d,2H,J = 3.9 Hz) | 4.13 | 4.14 |
| OMe (s,3H) | 3.34 | 3.34 |
| OMe (s,3H) | 3.31 | 3.31 |

As far as the applicant is aware, these products are not described in the literature.

Example 2

Bis-1,3-(2,2-dibutoxy-1-hydroxyethyl)-2-imidazolidinone 860 mg (10 mmoles) of ethyleneurea (2-imidazolidinone) and 3.76 g (20 mmoles) of dibutoxyethanal were dissolved, under agitation at 40° C., in 4 g of acetone. The solution obtained was then brought to a slightly alkaline pH by addition of several drops of 2N caustic soda, then heated under agitation for 30 minutes at 30° C. and finally vacuum concentrated. The residual oil was then purified by chromatography on silica gel with ethyl acetate eluent. Two fractions were isolated: the first contained a product having an Rf of 0.6 and the second a product having an Rf of 0.45.

After elimination of the elution solvent, two oily products were isolated, corresponding to the two expected diastereoisomers of bis-1,3-(2,2-dibutoxy-1-hydroxyethyl)-2-imidazolidinone.

Physical analyses

| ¹H NMR, 200 MHz (DMSO $d_6$) | | |
|---|---|---|
|  | 1st isomer, ppm | 2nd isomer, ppm |
| OH (d,2H,J = 6 Hz) | 5.82 | 5.79 |
| N—CH—O (t,2H,J = 6 Hz) | 5.06 | 5.06 |
| CH (OBu)₂(d,2H,J = 6 Hz) | 4.40 | 4.36 |
| OCH₂ and NCH₂ (m,12H) | 3.6–3.23 | 3.6–3.23 |
| CH₂ (m,16H) | 1.57–1.25 | 1.53–1.24 |
| CH₃ (m,12H) | 0.92–0.83 | 0.92–0.82 |

¹³C NMR, 200 MHz (DMSO-$d_6$)

| 1st isomer, ppm | 2nd isomer, ppm |
|---|---|
| 159.4  C=O | 158.7  C=O |

-continued

| 1st isomer, ppm | | 2nd isomer, ppm | |
|---|---|---|---|
| 101.6 | CH(O/O) | 101.5 | CH(O/O) |
| 75.0 | NHCHOH | 74.9 | N—CHOH |
| 66.3 | O—CH$_2$— | 66.3 | O—CH$_2$— |
| 65.5 | O—CH$_2$— | 65.1 | O—CH$_2$— |
| 37.2 | N—CH$_2$— | 37.2 | N—CH$_2$— |
| 31.5 | —CH$_2$— | 31.5 | —CH$_2$— |
| 18.8 | —CH$_2$— | 18.8 | —CH$_2$— |
| 13.7 | —CH$_3$ | 13.7 | —CH$_3$ |

The spectra were in agreement with the proposed structure. As far as the applicant is aware, these products are not described in the literature.

Example 3 bis-1,3-(1,2,2-tributoxyethyl)-2-imidazolidinone 860 mg (10 mmoles) of ethyleneurea and 3.765 g (20 mmoles) of dibutoxyethanal were dissolved, under agitation at 40° C., in 4 g acetone. The solution obtained was then brought to a slightly alkaline pH by addition of several drops of 2N caustic soda then heated under agitation for 30 minutes at 30° C. and finally vacuum concentrated. The residual oil was acidified with several drops of 50% sulphuric acid in water and was then left for 2 hours under agitation at room temperature before being poured into 100 g water. The aqueous phase was decanted and washed three times with 50 g hexane, the organic phases added together and washed with 1N caustic soda then water until the washings were neutral, then finally dried over anhydrous calcium chloride, filtered and vacuum dried. The crude residual oil was subsequently purified by silica gel chromatography using ethyl acetate as eluent. 3.43 g (6 mmoles) of bis-1,3-(1,2,2-tributoxyethyl)-2-imidazolinone was obtained in this fashion as a colourless oil which was soluble in hexane and in diisopropyl oxide.

This product was the expected mixture of the two disastereoisomers.

Physical analysis

| 1 - $^1$H NMR, CDCl$_3$ (deuterated chloroform) | | |
|---|---|---|
| | 1st isomer, ppm | 2nd isomer, ppm |
| N—CH—O (d,2H) | 5.16 (J = 5.9 Hz) | 5.15 (J = 5.6 Hz) |
| CH (OBu)$_2$(d,2H) | 4.52 (J = 5.9 Hz) | 4.51 (J = 5.6 Hz) |
| OCH$_2$ and NCH$_2$ (m,16H) | 3.63–3.41 | |
| CH$_2$ (m,24H) | 1.61–1.29 | |
| CH$_3$ (m,12H) | 0.95–0.86 | |

| 2-$^{13}$C NMR, CDCl$_3$ | 1st isomer, ppm | 2nd isomer, ppm |
|---|---|---|
| \C=O / | 160.42 | 160.35 |
| —CH (OBu)$_2$ | 100.8 | 100.9 |
| N—CH—OBu | 81.7 | 81.8 |
| OCH$_2$ | 68.1–68.0 — 67.1–67.0 | |
| | 65.5 and 65.4 | |
| N—CH$_2$ | 37.7 | 37.9 |
| CH$_2$ | 31.9–31.8 — 31.5–19.3 | |

| 2-$^{13}$C NMR, CDCl$_3$ | 1st isomer, ppm | 2nd isomer, ppm |
|---|---|---|
| CH$_3$ | 13.8 | |

As far as the applicant is aware, these products are not described in the literature.

Example 4 bis-1,3-(2,2-diethoxy-1-hydroxyethyl)2-imidazolidinone 45 g (0.34 mole) of diethoxyethanal and 14.6 g (0.17 mole) of ethyleneurea were heated together, under agitation, for one hour at 65°±5° C. at a slightly alkaline pH.

On cooling, the desired product crystallised out spontaneously. It was recrystallised from diisopropyl oxide to give 50.6 g (0.144 mole) of bis-1,3-(2,2-diethoxy-1-hydroxyethyl)-2-imidazolidinone as colourless crystals having a melting point of 105° C., 85% of theoretical yield.

Microanalysis

| | | C % | H % | N % | O % |
|---|---|---|---|---|---|
| C$_{15}$H$_{30}$N$_2$O$_7$ | Calculated | 51.41 | 8.63 | 8.0 | 31.96 |
| M. Wt 350.4 | Found | 51.3 | 8.7 | 8.0 | |

Analysis using thin layer chromatography on silica gel with a 95:5 dichloromethane-methanol eluent showed the presence of two products having respective Rf values of 0.16 and 0.21. Following isolation using preparative HPLC, these two products had the following NMR spectra:

| 1 - $^1$H NMR, DMSO d$_6$ | | |
|---|---|---|
| | 1st isomer, ppm | 2nd isomer, ppm |
| OH (d,2H,J = 6.0 Hz) | 5.85 | 5.81 |
| N—CH—O (t,2H,J = 6.0 Hz) | 5.04 | 5.04 |
| CH (OEt)$_2$(d,2H,J = 6.0 Hz) | 4.41 | 4.41 |
| —CH$_2$— (m,12H) | 3.69–3.25 | |
| —CH$_3$— (m,12H) | 1.17–1.05 | |

2 - $^{13}$C NMR, DMSOd$_6$

| | 1st isomer, ppm | 2nd isomer, ppm |
|---|---|---|
| C=O | 159.4 | 158.6 |
| CH(O/O) | 101.4 | 101.2 |
| N—CH—O | 75.1 | 74.9 |
| OCH$_2$ | 62.2 | 62.2 |
| OCH$_2$ | 61.4 | 61.0 |
| N—CH$_2$ | 37.1 | 37.1 |
| CH$_3$ | 15.3 | 15.3 |

As far as the applicant is aware, this product is not described in the literature.

Example 5 bis-1,3-(2,2-dimethoxy-1-hydroxyethyl)-2-imidazolidinone 292.5 g (2 moles) of dimethoxyethanal, in a 53% by weight solution in water, was heated, with agitation, for one hour at 50° C. with 86 g (1 mole) of ethyleneurea and a sufficient amount of 2N caustic soda to produce a pH of 8.

The solution obtained was vacuum concentrated. The desired product crystallised out spontaneously. After taking up in diethyl oxide and vacuum drying to constant weight at 40° C., 262 g (0.89 mole) of crystalline bis-1,3-(2,2-diomethoxy-1-hydroxyethyl)-2-imidazolidinone having a melting point of 127°±3° C. were isolated.

Microanalysis

|  |  | C % | H % | N % | O % |
|---|---|---|---|---|---|
| $C_{11}H_{22}N_2O_7$ | Calculated | 44.89 | 7.54 | 9.52 | 38.05 |
| M. Wt = 294.31 | Found | 44.8 | 7.7 | 9.6 |  |
| $^{13}$C NMR, DMSO $d_6$ |  |  |  |  |  |

|  | ppm |
|---|---|
| C=O | 159.2 |
| —CH (OMe)$_2$ | 103.1 |
| N—CH—O | 74.5 |
| O—CH$_3$ | 54.2 |
| O—CH$_3$ | 53.6 |
| O—CH$_2$ | 36.7 |

A far as the applicant is aware, this product is not described in the literature.

Example 6 bis-1,3-(1,2,2-trimethoxyethyl)-2-imidazolidinone

A solution of 40.8 g (0.125 mole) bis-1,3-(2,2-dimethoxy-1-hydroxyethyl)-2-imidazolidinone in 85 g methanol and a sufficient amount of sulphuric acid, 25 weight percent in water, to bring it to pH=4 was agitated and heated for 90 minutes at 50° C.

The solution obtained was cooled to room temperature, neutralised to pH=7 with sodium bicarbonate and dried under vacuum. The crystalline product was hot-cold recrystallised from dipropyl oxide.

36.3 g (0.1125 mole) of crystalline bis-1,3-(1,2,2-triethoxyethyl)-2-imidazolidinone were obtained, having a melting point of 66°±3° C.

Microanalysis

|  |  | C % | H % | N % | O % |
|---|---|---|---|---|---|
| $C_{13}H_{26}N_2O_7$ | Calculated | 48.4 | 8.13 | 8.69 | 34.74 |
| M. Wt = 322.4 | Found | 48.3 | 8.2 | 8.7 |  |

As far as the applicant is aware, this product is not described in the literature.

Example 7 bis-1,3-(2,2-dimethoxy-1-hydroxyethyl)-4,5-dihydroxy-2-imidazolidinone 29.5 g (0.25 mole) of the trans isomer of 4-5-dihydroxy-2-imidazolidinone was dissolved, under agitation at 50° C., in 104 g of dimethoxyethanal at 59 weight percent aqueous solution, i.e. 0.5 mole, and the solution obtained brought to pH=8–9 by addition of several drops of 2N caustic soda. The solution was then heated for one hour at 50° C., under agitation, then vacuum concentrated.

The residual oil was subsequently purified using silica gel chromatography using a dichloromethanemethanol mixture as eluent. 40.7 g (0.125 mole) of bis-1,3-(2,2-dimethoxy-1-hydroxyethyl)-4,5-dihydroxy-2-imidazolidinone were thus obtained as a colourless oil whose $^1$H NMR and $^{13}$C NMR spectra were in agreement with the proposed structure.

Microanalysis

|  |  | C % | H % | N % | O % |
|---|---|---|---|---|---|
| $C_{11}H_{22}N_2O_9$ | Calculated | 40.49 | 6.79 | 8.59 | 44.13 |
| M. Wt = 326.3 | Found | 39.8 | 6.9 | 8.4 |  |

As far as the applicant is aware, this product is not described in the literature.

Example 8

Bleached and whitened 100% cotton poplin fabric having a weight of approximately 130 g per square meter was impregnated by sizing with a squeezing ratio of 75% in a bath containing, in solution:

0.4534 moles per liter of a substituted urea according to the present invention;

12 g per liter magnesium chloride hexahydrate;

2.1 g per liter acetic acid;

2 g per liter ethoxylated nonyphenol with 10 moles of ethylene oxide.

The fabric was dried at 120° C. then underwent thermal treatment at 180° C. for 35 seconds on a laboratory tenter.

Samples of the treated fabric were used to determine:

crease removability according to AATCC No. 66-1973 measured on samples as treated and on samples which had been given three domestic 60° C. washes; crease removability is expressed as the sum of the crease angles obtained in the warp and weft direction;

traction resistance, expressed in daN, in the warp and weft directions according to the AFNOR G07 001 standard;

the residual formaldehyde ratio, Tfr, in the fabric according to the method in AATCC 112-1982 and according to the method described in the Japanese law No. 112-1973.

The results obtained are given in Table I:

TABLE I

|  | Crease angles on fabric: | | | |
|---|---|---|---|---|
|  | as such | after 3 washes | $R_t$ | $T_{fr}$ |
| untreated fabric fabric | 174 | 174 | 98.4 | undetectable |
| treated with product from example 5 fabric | 273 | 248.5 | 63.1 | undetectable |
| treated with product from example 6 | 271 | 248 | 50.5 | undetectable |

It can be seen that the products of the present invention considerably improve the crease resistant properties of the treated fabrics.

We claim:

1. A urea in its racemic form or a mixture of stereoisomers of the formula

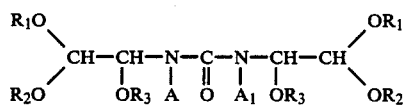

in which either $R_1$ and $R_2$ are identical and represent the —$CH_2R$ group where R represents a hydrogen atom or a $C_1$ to $C_4$ alkyl radical, or $R_1$ and $R_2$ together form a —$CH_2$—$(CR_4R_4)n$—$CH_2$ group in which n is 0 or 1 and $R_4$ represents a hydrogen atom or methyl group, $R_3$ represents a hydrogen atom or a —$CH_2R_5$ radical in which $R_5$ represents a hydrogen atom or a $C_1$ to $C_4$ alkyl group and either A and $A_1$ are identical and represent a hydrogen atom or A and $A_1$ together form an ethylene, trimethylene or —$CH(OCH_2R_6)$—$CH(OCH_2R_6)$— radical wherein $R_6$ represents hydrogen atom or a $C_1$ to $C_4$ alkyl group or, where R3 represents a hydrogen atom, or a 1,2-dihydroxyethylene group.

2. A urea as defined in claim 1, characterised in that, in formula I, $R_1$ and $R_2$ are identical and represent a methyl or butyl group, $R_3$ represents a hydrogen atom, a methyl group or a butyl group, and either A and $A_1$ are identical and represent a hydrogen atom or A and $A_1$ together form an ethylene group, a 1-2-dimethoxyethylene group, a 1,2-dibutoxyethylene group or, where $R_3$ represents a hydrogen atom, a 1,2-dihydroxyethylene group.

3. A urea corresponding to formula I of claim 1, which is bis-1,3-(2,2 dimethoxy-1-hydroxyethyl)-Urea.

4. A urea corresponding to formula I of claim 1, which is bis-1,3 (1,2,2-trimethoxyethyl) Urea.

5. A urea corresponding to formula I of claim 1, which is bis-1,3-(2,2-dimethoxy-1-hydroxyethyl)-2-imidazolidinone.

6. A urea corresponding to formula I of claim 1, which is bis-1,3-(1,2,2-trimethoxyethyl)-2-imidazolidinone.

7. A urea corresponding to formula I of claim 1, which is bis-1,3-(2,2-butoxy-1-hydroxy-ethyl)-2-imidazolidinone.

8. A urea corresponding to formula I of claim 1, which is bis-1,3-(1,2,2-tributoxyethyl)-2-imidazolidinone.

9. A urea corresponding to formula I of claim 1, which is bis-1,3-(2,2-diethoxy-1-hydroxyethyl)-2-imidazolidinone.

10. A urea corresponding to formula I of claim 1, which is bis-1,3-(2,2-dimethoxy-1-hydroxyethyl)-4,5-dihydroxy-2-imidazolidinone.

11. In a method for the treatment of cellulose fibres or fabrics to endow said fibres and fabrics with crease and shrink resisting properties, comprising treating said fibres or fabrics with a cross-linking agent, the improvement wherein said cross-linking agent comprises a product of formula I in accordance with claim 1.

12. In a method for the treatment of cellulose fibres or fabrics to endow said fibres and fabrics with crease and shrink resisting properties, comprising treating said fibres or fabrics with a cross-linking agent, the improvement wherein said cross-linking agent comprises a product of formula I in accordance with claim 2.

* * * * *